(12) United States Patent
Groll et al.

(10) Patent No.: US 8,398,443 B2
(45) Date of Patent: Mar. 19, 2013

(54) BIOLOGICAL TESTING SYSTEM AND CONNECTOR THEREFOR

(75) Inventors: Henning Groll, Indianapolis, IN (US); Michael J. Celentano, Fishers, IN (US); Joseph A. Finnerty, Canfield, OH (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1253 days.

(21) Appl. No.: 11/612,190

(22) Filed: Dec. 18, 2006

(65) Prior Publication Data

US 2007/0249921 A1    Oct. 25, 2007

Related U.S. Application Data

(63) Continuation of application No. 11/409,383, filed on Apr. 21, 2006, now abandoned.

(51) Int. Cl.
*H01R 4/48* (2006.01)
(52) U.S. Cl. ........................ 439/862; 439/909
(58) Field of Classification Search .................. 439/862, 439/260, 852, 629, 630, 636, 637, 909, 845, 439/843, 842, 847, 850, 748, 856, 857
See application file for complete search history.

(56) References Cited

U.S. PATENT DOCUMENTS

| | | | | |
|---|---|---|---|---|
| 3,474,380 A | * | 10/1969 | Miller | 439/752 |
| 3,555,497 A | * | 1/1971 | Watanabe | 439/857 |
| 3,567,998 A | | 3/1971 | Ammerman | |
| 3,851,297 A | * | 11/1974 | Munro | 439/591 |
| 4,008,448 A | | 2/1977 | Muggli | |
| 4,225,410 A | | 9/1980 | Pace | |
| 4,233,029 A | | 11/1980 | Columbus | |
| 4,323,536 A | | 4/1982 | Columbus | |
| 4,367,006 A | | 1/1983 | Rehbogen, Jr. et al. | |
| 4,420,215 A | * | 12/1983 | Tengler | 439/723 |
| 4,503,609 A | | 3/1985 | Mackay | |
| 4,560,231 A | * | 12/1985 | Shirai | 439/843 |
| 4,654,197 A | | 3/1987 | Lilja et al. | |
| 4,752,254 A | * | 6/1988 | Inoue et al. | 439/834 |
| 4,826,445 A | | 5/1989 | Verhoeven et al. | |
| 4,919,770 A | | 4/1990 | Preidel et al. | |
| 4,934,961 A | | 6/1990 | Piorunneck et al. | |
| 4,973,270 A | | 11/1990 | Billman et al. | |
| 4,996,766 A | | 3/1991 | Piorunneck et al. | |

(Continued)

FOREIGN PATENT DOCUMENTS

| EP | 0 523 463 | 1/1993 |
|---|---|---|
| EP | 0 523 463 A2 | 1/1993 |

(Continued)

*Primary Examiner* — Tho D Ta
(74) *Attorney, Agent, or Firm* — Woodard, Emhardt, Moriarty, McNet & Henry LLP

(57) ABSTRACT

A connector for establishing electrical connection between a testing device and a test strip with a biological fluid thereon includes a contact pad on the test strip, and one or more contact wires in the testing device. When the strip is inserted into the testing device, part of the strip's end engages a contact portion of a contact wire and deflects it in a direction normal to the direction of insertion. In certain embodiments the radius of curvature (in the direction of insertion) of the contact portion is controlled to reduce abrasion of the strip by the wire. In other embodiments the radius of curvature (perpendicular to the direction of insertion) is controlled to reduce the abrasion of the strip by the wire. Sometimes the contact portion and/or contact pad is plated with a sacrificial material to reduce the coefficient of friction. In other embodiments various numbers of contacts receive the end of the strip substantially simultaneously, or are staggered in rows to distribute the resistance presented.

110 Claims, 12 Drawing Sheets

U.S. PATENT DOCUMENTS

| | | | |
|---|---|---|---|
| 5,015,197 A * | 5/1991 | Redmond et al. | 439/329 |
| 5,024,609 A | 6/1991 | Piorunneck | |
| 5,049,511 A * | 9/1991 | Yu | 439/325 |
| 5,108,564 A | 4/1992 | Szuminsky et al. | |
| 5,120,420 A | 6/1992 | Nankai et al. | |
| 5,128,015 A | 7/1992 | Szuminsky et al. | |
| 5,243,516 A | 9/1993 | White | |
| 5,288,636 A | 2/1994 | Pollmann et al. | |
| 5,437,999 A | 8/1995 | Diebold et al. | |
| 5,628,890 A | 5/1997 | Carter et al. | |
| 5,679,018 A | 10/1997 | Lopata et al. | |
| 5,682,884 A | 11/1997 | Hill et al. | |
| 5,727,548 A | 3/1998 | Hill et al. | |
| 5,997,817 A | 12/1999 | Crismore et al. | |
| 6,004,441 A | 12/1999 | Fujiwara et al. | |
| 6,017,246 A | 1/2000 | Hisazumi et al. | |
| 6,036,519 A | 3/2000 | Lopata et al. | |
| 6,054,039 A | 4/2000 | Shieh | |
| 6,149,466 A * | 11/2000 | Bricaud et al. | 439/630 |
| 6,379,513 B1 | 4/2002 | Chambers et al. | |
| 6,568,955 B2 * | 5/2003 | Hotea et al. | 439/495 |
| 7,641,777 B2 * | 1/2010 | Joseph et al. | 204/406 |
| 2003/0155237 A1 | 8/2003 | Surridge et al. | |
| 2003/0203498 A1 | 10/2003 | Neel et al. | |
| 2004/0005716 A9 | 1/2004 | Beaty et al. | |
| 2004/0157337 A1 | 8/2004 | Burke et al. | |
| 2004/0157338 A1 | 8/2004 | Burke et al. | |
| 2004/0157339 A1 | 8/2004 | Burke et al. | |
| 2004/0256248 A1 | 12/2004 | Burke et al. | |
| 2004/0259180 A1 | 12/2004 | Burke et al. | |
| 2004/0260511 A1 | 12/2004 | Burke et al. | |
| 2005/0013731 A1 | 1/2005 | Burke et al. | |
| 2006/0052682 A1 | 3/2006 | Joseph et al. | |
| 2006/0156796 A1 | 7/2006 | Burke et al. | |

FOREIGN PATENT DOCUMENTS

| | | |
|---|---|---|
| EP | 0 645 626 | 3/1995 |
| EP | 0 645 626 A1 | 3/1995 |
| WO | WO 98/43073 A | 10/1998 |
| WO | WO 2006/027222 A | 3/2006 |

* cited by examiner

BIOLOGICAL TESTING SYSTEM AND CONNECTOR THEREFOR

PRIORITY CLAIM

This patent application is a continuation of U.S. Ser. No. 11/409,383, filed on Apr. 21, 2006, now abandoned which is incorporated herein by reference in its entirety.

TECHNICAL FIELD OF THE INVENTION

The present invention relates to testing apparatus for testing the presence or concentration of one or more substances in a biological fluid, and more particularly to such a device that includes one or more electrical connections between a test strip (bearing a sample of the biological fluid) and a test meter.

BACKGROUND OF THE INVENTION

Measuring the concentration of substances, particularly in the presence of other substances, is important in many fields. This is especially true in medical testing and diagnosis. For example, the measurement of glucose in body fluids, such as blood, is crucial to the effective treatment of diabetes.

Multiple methods are known for measuring the concentration of analytes, for example glucose, in a blood sample. Such methods typically fall into one of two categories: optical methods and electrochemical methods. Optical methods generally involve reflectance or absorbance spectroscopy to observe the spectrum shift in a reagent. Such shifts are caused by a chemical reaction that produces a color change indicative of the concentration of the analyte. Electrochemical methods generally involve, alternatively, amperometric or coulometric responses indicative of the concentration of the analyte. See, for example, U.S. Pat. No. 4,233,029 to Columbus, U.S. Pat. No. 4,225,410 to Pace, U.S. Pat. No. 4,323,536 to Columbus, U.S. Pat. No. 4,008,448 to Muggli, U.S. Pat. No. 4,654,197 to Lilja et al., U.S. Pat. No. 5,108,564 to Szuminsky et al., U.S. Pat. No. 5,120,420 to Nankai et al., U.S. Pat. No. 5,128,015 to Szuminsky et al., U.S. Pat. No. 5,243,516 to White, U.S. Pat. No. 5,437,999 to Diebold et al., U.S. Pat. No. 5,288,636 to Pollmann et al., U.S. Pat. No. 5,628,890 to Carter et al., U.S. Pat. No. 5,682,884 to Hill et al., U.S. Pat. No. 5,727,548 to Hill et al., U.S. Pat. No. 5,997,817 to Crismore et al., U.S. Pat. No. 6,004,441 to Fujiwara et al., U.S. Pat. No. 4,919,770 to Priedel, et al., and U.S. Pat. No. 6,054,039 to Shieh, which are hereby incorporated in their entireties.

A sample-receiving portion of the testing apparatus typically controls the geometry of the blood sample. In the case of blood glucose meters, for example, the blood sample is typically placed onto or into a disposable test strip that is inserted into a test meter. In the case of electrochemical test meters, electrical signals must be transferred between the meter and the test strip and vice versa.

Test system designers desire to minimize the size of the sample required for accurate measurement in order to improve the user experience. The resulting test sensor and test strip miniaturization has resulted in the use of thin film test strip patterns comprised of noble metals deposited on plastic substrates, such as by plating and subsequent laser ablation, to form the electrodes and associated connector contact pads of the test strip. These techniques allow for improved edge quality and improved dimensional resolution of the metallized features on the test strip. Such thin film coatings are highly prone to scratching by current commercially available connectors. Therefore, reducing abrasion between the test strip contact pad and meter connector contact wire is especially important in biosensor designs. Repeat insertions of the test strip (two to four times) can render these thin film-coated biosensors useless. Even the first-time insertion of the test strip into the test meter may cause some removal of these thin film coatings by the test meter connector. The result is a less reliable connection between the contact pad on a test strip and the connector contact wire in the test meter.

Reducing abrasion between the test strip contact pad and meter connector contact wire is also important for longevity of the test meter. A typical test meter may have a life cycle requirement of over 10,000 test strip insertions. During normal use, a single test strip may be inserted and removed from the meter several times before the test is successfully performed. Abrasive contact between the connector contact wire and contact pad can reduce the longevity of the test meter connector, thereby further reducing the reliability of the system. Some biosensor systems are designed for use by consumers, who sometimes put still further stresses on the test system by using the system in environments at the margins of its design specifications, such as in high-humidity environments, or exposing the device to air containing corrosive components.

Thus, there is a need for further contributions and improvements to biosensor system technology, including connectors that provide improved performance and resistance to abrasion of test strip contact pads and meter connector contact wires.

SUMMARY OF THE INVENTION

Some forms of the present invention improve user experience by increasing the probability of the test meter connector making a reliable contact with the inserted test strip. One form includes a system for measuring an analyte of interest in a biological fluid, where a connector provides an interface between a test strip bearing the biological fluid and a test meter. The analyte of interest is applied to a test strip having at least one contact pad for mating with the connector when the test strip is inserted through an opening in the meter housing. The connector comprises at least one contact wire disposed within the housing, where each contact wire has a distal portion and a proximal portion. The contact wire's proximal portion engages the connector housing and anchors the distal portion to the connector housing. The contact wire contacts the test strip upon insertion.

Initially, the contact wire is in a resting position relative to the connector housing. As the test strip is moved into the connector opening it touches the contact wire. Upon further insertion, the test strip creates a normal force acting upon the contact wire's distal portion. The normal force deflects the contact wire from its resting position and flexes portions of the contact wire in a spring fashion. Further insertion of the test strip causes the contact wire's distal portion to come into electrical contact with the contact pad. When the test strip is fully inserted, the contact wire squeezes the test trip between the contact portion of the contact wire and the connector housing. The test strip is withdrawn after the system performs the desired test. The contact wire returns to its resting position once the contact wire is no longer in contact with the test strip.

Another form of the invention is a testing system comprising a meter (including a housing, a connector, and an electronic circuit) and a test strip. The electronic circuit produces an output signal corresponding to the presence or concentration of an analyte in a sample of bodily fluid that is in contact with the test strip inserted into the connector. At least one embodiment of this form includes a connector having one or more contact wires. Each contact wire is configured to allow the contact wire to engage a contact pad on a test strip and communicate with the test system. Further, when a test strip is inserted into the connector, the test strip exerts a force against the contact wire that is substantially normal to the direction of insertion to allow the contact wire to engage the contact pad.

Yet another embodiment of the present invention is a device for testing an analyte on a test strip, comprising a connector having a plurality of contact wires. The proximal portion of each contact wire is fixed at least at one point within a connector housing. Part of the distal portion of each contact wire has a concave shape. In other embodiments, the contact wire has a convex-shaped portion. The "contact portion" of the contact wire that engages the test strip or contact pad has a desired radius of curvature, which may be at least about 3 mm, 4 mm, or 6 mm. Controlling the contact portion's radius of curvature reduces the frictional force that develops between the contact wire and test strip during insertion and removal, and minimizes the resulting abrasion.

Still other embodiments of the present invention include features and techniques for extending, rounding, or smoothing the end of the contact portion of the contact wire in the direction of insertion. Certain embodiments include a distal portion that has a cantilevered form and a contact portion that extends in the direction of test strip extraction. Certain other embodiments include a distal portion that has a cantilevered form and a contact portion that extends in the direction of test strip insertion.

Some embodiments further include rounding or smoothing the radius of curvature of the contact wire perpendicular to the direction of test strip insertion. Other embodiments of the present invention include a technique of plating the contact portion of the contact wire with soft, electrically conductive materials that are sacrificed during the test strip insertion and extraction process to minimize abrasion of the contact pad and other parts of the test strip. In certain other embodiments, the contact portion is plated with a non-gold material. Some embodiments include contact wires plated with soft metallic materials, and the wires each have a contact portion with a relatively small radius of curvature. In at least one such embodiment, a contact portion plated with a soft sacrificial material has a minimum radius of curvature less than 1 mm. Still other embodiments include techniques and features to minimize the normal force applied to the test strip by the distal portion during test strip insertion and extraction.

Other embodiments of the present invention include a minimally abrading connector comprising a single-piece connector housing and n contact wires held in a substantially rigid relationship. When the test strip is inserted into the connector, the n contact wires establish electrical contacts with the test strip's contact pads. Some embodiments have a further feature of staggering the position of the n contact wires in two, three, or more rows to increase the density of contact pad placement on test strips.

Certain embodiments of the present invention include contact wires having a distal end. In certain of these embodiments, the distal end is approximately loop-shaped. In certain of these embodiments, the distal end distributes energy imparted to the contact wire from friction with a test strip generates force distributed through directions that span at least 90 degrees. In certain of these embodiments, the distal end of the contact wires are formed to avoid positive feedback in frictional forces between the contact wires and the test strip.

DETAILED DESCRIPTION OF THE PREFERRED EMBODIMENTS

Figure 1:
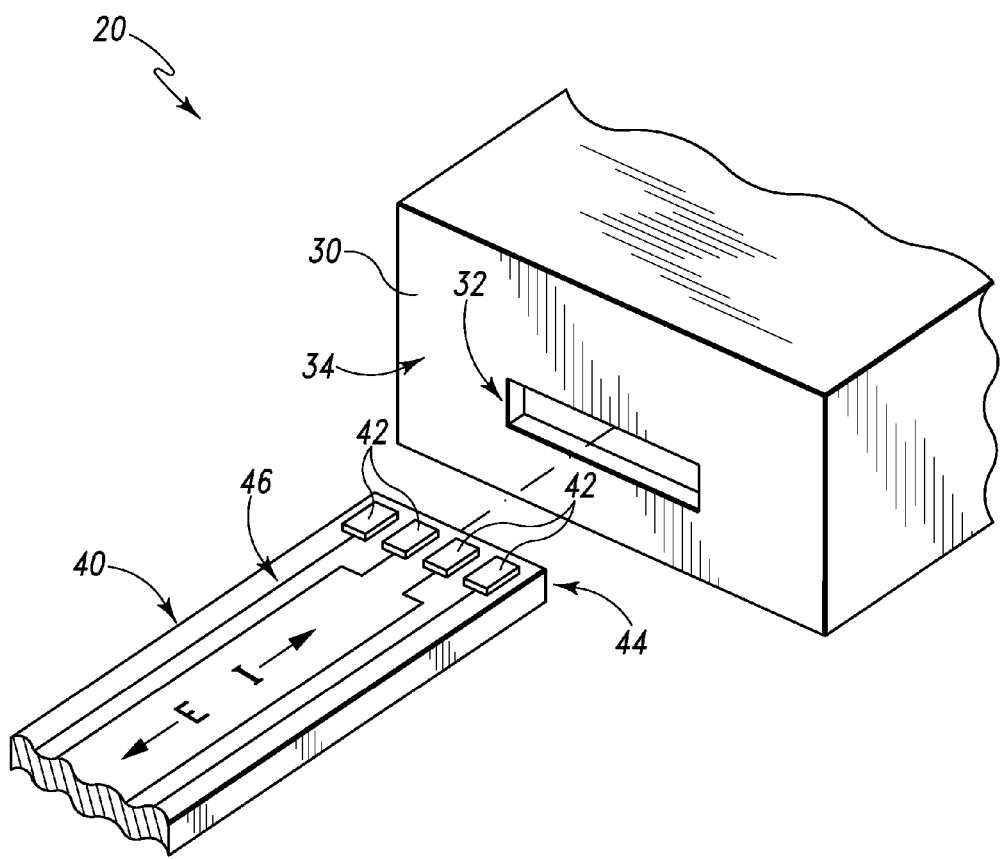
FIG. 1 is a perspective view of a biological testing system according to one embodiment of the present invention.

For the purpose of promoting an understanding of the principles of the present invention, reference will now be made to the embodiment illustrated in the drawings and specific language will be used to describe the same. It will, nevertheless, be understood that no limitation of the scope of the invention is thereby intended; any alterations and further modifications of the described or illustrated embodiments, and any further applications of the principles of the invention as illustrated therein are contemplated as would normally occur to one skilled in the art to which the invention relates.

A system for testing blood according to the present invention enables greater contact density with higher reliability on thin film metallized plastic substrates. These higher densities enable one to include additional electrodes that are used in some embodiments to assure the measurement accuracy and reliability for supporting a fast, small volume test. Smaller samples, in turn, make blood testing easier and less uncomfortable. This can mean a significant improvement in the standard of living, especially for people who require regular blood testing, such as diabetics.

Smaller sample sizes with equivalent reliability are achieved through increased density of measurement electrodes. Recent improvements in laser ablation techniques for the manufacture of medical test strips have significantly increased the resolution and fineness of metallized contact pad and connector trace geometries on test strips. While this innovation has enabled more contacts to be placed in a given area, the resulting detailed and delicate structures are susceptible to abrasive damage. As a result, measurement reliability is threatened. In order to preserve measurement reliability, a less abrasive connection system, and techniques minimizing test strip abrasion during insertion and extraction, are needed. Embodiments of the present invention provide a significant improvement in this aspect of the art.

The present invention minimizes or eliminates abrasion of test strip contact pads formed of a thin layer of metal when the test strip is inserted into a test meter. Little or no damage to the test strip thin film surface by the connector, nor to the connector contact wire by the test strip, occurs in some embodiments of the present invention due to the contact wire of the connector being formed with a rounded surface in one or more dimensions.

Generally, exemplary biological testing system 20 shown in FIG. 1 includes a reusable testing meter 30 having an end 34. A disposable test strip 40 is inserted in direction I through slot 32 in end 34. Strip 40 includes at least one contact pad 42 (four such contact pads are shown in FIG. 1 by way of example only) near its end 44. These contact pads are connected via conductors 46 to electrodes (not shown) near the end of strip 40 opposite end 44 (i.e., near the end in the direction indicated by directional arrow E). As a non-limiting example, one embodiment has four contact pads connected to four electrodes. Other embodiments of the invention may include more or fewer contact pads or electrodes, different numbers and patterns of conductor traces 46, and/or different numbers of electrodes on a given test strip 40. The test strip 40 is inserted into testing device 30 in insertion direction I.

Figure 2:
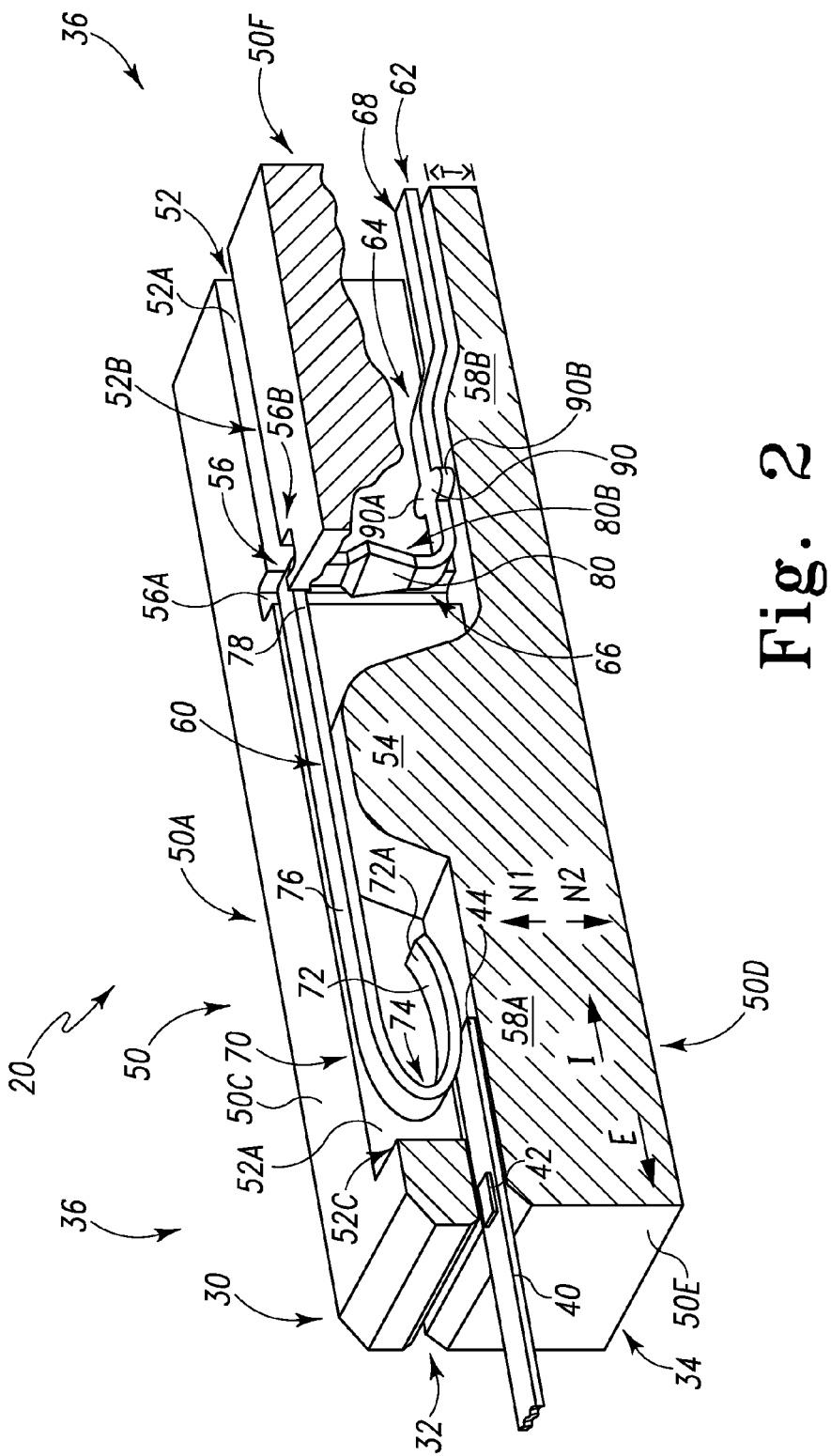
FIG. 2 is a sectional view of a connector according to one embodiment of the invention.

As illustrated in the cutaway view of assembly 36 shown in FIG. 2, in one embodiment of the present invention, system 20 receives a test strip 40 inserted through slot 32 into testing device 30 by movement of the test strip 40 in direction B. Slot 32 in testing device 30 may comprise an end of a connector housing for receiving the test strip 40 or, alternatively, slot 32 may simply be an opening in testing device 30 situated adjacent to the connector housing. The connector housing 50 includes first side 50A and a second side (opposite first side 50A and not visible in the sectional view of FIG. 2), top 50C, base 50D, front 50E, and back 50F. Connector housing 50 additionally defines wire slot 52 and assembly slot 56 therein.

As described hereinabove, the front side 50E includes an opening for slot 32, a corridor for passing test strips 40 through front side 50E to the region of wire slot 52. As an additional, optional feature, the opening of slot 32 on front 50E may include beveling as shown to help guide test strip 40 into slot 32. Assembly slot 56 has first assembly feature 56A and second assembly feature 56B (opposite of first assembly feature 56A). Assembly features 56A and 56B provide a path through which alignment portion 80 of contact wire 60 is passed when the connector assembly 36 is being assembled, as described in greater detail hereinbelow.

Wire slot 52 extends into housing 50 in the direction of insertion I for test strip 40, and has a width in direction N1. Wire slot 52 is defined by first wire slot wall 52A, second wire slot wall 52B (opposite first wire slot wall 52A), front wire slot wall 52C, back 50F, projection 54, first wire slot floor 58A, second wire slot floor 58B, and top 50A.

The floor of wire slot 52 comprises first wire slot floor 58A, projection 54, and second wire slot floor 58B. First wire slot floor 58A extends to a first plane approximately normal to wire slot walls 52A and 52B and connects first wire slot wall 52A and second wire slot wall 52B. Second wire slot floor 58B extends to at least one second plane substantially normal to wire slot walls 52A and 52B and connects first and second wire slot walls 52A and 52B. Protrusion 54 connects the first wire slot floor 58A to second wire slot floor 58B and connects first wire slot wall 52A and second wire slot wall 52B. Wire slot 52 may further include front wall 52C of some thickness that lies in a plane substantially normal to first wire slot floor 58A and connects to first wire slot wall 52A and second wire slot wall 52B.

The opening of slot 32 into wire slot 52 is defined by a gap between front wire slot wall 52C and wire slot floor 58A. In some embodiments, the connector housing back 50F provides an opening for the contact wire 60 to pass through housing back 50F. In other embodiments, as shown in FIG. 2, a portion of the wire slot 52 extends to the back 50F and creates an opening for the contact wire 60 to pass through back 50F. Although FIG. 2 shows a connector assembly comprising a connector housing 50 having a single wire slot 52 for accepting a single contact wire 60, it is understood that this is for illustrative purposes and that other embodiments having multiple contact wires and wire slots or multiple contact wires per wire slot are contemplated.

In some embodiments, first wire slot floor 58A and second wire slot floor 58B are coplanar. In other embodiments, first wire slot floor 58A and second wire slot floor 58B lie in different planes. In still other embodiments, as shown in FIG. 2, second wire slot floor 58B is shaped or angled to provide a multi-planar transition from protrusion 54 to the connector back 50F.

In the embodiment illustrated in FIG. 2, connector assembly 36 is formed by placing contact wire 60, having a distal portion 70 and proximal portion 62, into wire slot 52 of connector housing 50. The distal portion 70 is placed in proximity with the first wire slot floor 58A, while the proximal portion 62 is placed in proximity with the second wire slot floor 58B. As test strip 40 is inserted, it passes through slot 32 and comes into contact with distal portion 70 of contact wire 60. The distal portion 70 includes portions of contact wire 60 that allow some freedom of movement or flexing in the normal directions N1 and N2 to permit test strip 40 to pass between the contact wire 60 and first wire slot floor 58A of the connector housing 50. While distal portion 70 flexes, proximal portion 62 remains in a substantially fixed position relative to the connector housing 50.

Figure 3:
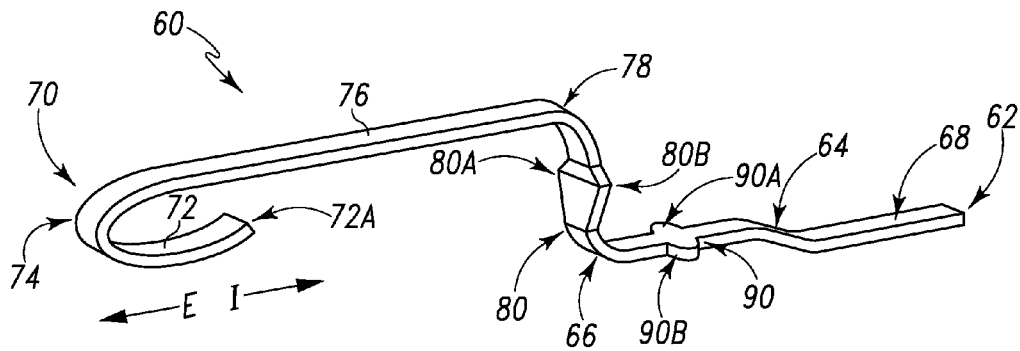
FIG. 3 is a perspective view of a contact wire according to one embodiment of present invention.

As illustrated in FIG. 3, one embodiment of the present invention has at least one contact wire 60 with a proximal portion 62 and a distal portion 70. Proximal portion 62, including the combination of alignment portion 80 and engaging portion 90, aligns and secures contact wire 60 within a connector housing assembly. Alignment portion 80 has features for aligning contact wire 60 in the connector housing. Alignment portion 80 includes a first protrusion 80A and second protrusion 80B adapted to interface with assembly slot 56. In at least one embodiment, alignment portion 80 includes features that are substantially keystone or coffin shaped. The alignment portion 80 can have alternative shapes or protrusions that provide improved engagement with assembly slot 56 and function to align contact wire 60 in the connector housing 50. The present invention includes those shapes and features that would be recognized by those skilled in the art as adapted for engaging assembly slot 56.

Similarly, some embodiments of engaging portion 90 have protrusions 90A and 90B to engage walls of wire slot 52. As a non-limiting example, engagement portion 90 can have a number of regular or irregular shapes. Other embodiments of engagement portion 90 have various shapes or features including tabs, edges, protrusions, and ridges that hold proximal end 62 in a fixed position within wire slot 52. Thus, the present invention includes those shapes and features that would be recognized by those skilled in the art as adapted for stable contact between engaging portion 90 and the walls or floor of wire slot 52.

Proximal portion 62 of wire 60 also includes end portion 68 to provide an electrical connection to the internal circuitry of the testing meter 30. The proximal portion 62 may further include as features wire segment 64 and curve segment 66.

Wire segment 64 and curve segment 66 work in combination with engaging portion 90 to provide a transition between alignment portion 80 and wire end 68. As shown in FIG. 2, curve segment 66 orients alignment portion 80 relative to engaging portion 90. Wire segment 64 is bent to position wire end 68 relative to engaging portion 90.

Distal portion 70, also shown in FIG. 3, includes contact portion 72, contact portion end 72A, transition portion 74, arm portion 76, and spring portion 78. As described below in greater detail, the distal portion 70 is used to create a backward-pointing or reverse-cantilevered structure relative to the proximal portion 62. The contact portion 72 provides a curved (i.e. radius of curvature in parallel planes) and/or spoon-shaped (i.e. radius of curvature in perpendicular planes), low-abrasive point of contact between the contact wire 60 and a test strip 40. As described below, spring portion 78 and arm portion 76 hold contact portion 72 in position for receiving the test strip 40. As a further feature, contact portion 72 and contact portion end 72A may be shaped or extended to minimize abrasion of the test strip 40 during insertion (and extraction) of the test strip 40 into (and out of) the meter 30.

Certain embodiments of the present invention combine the functionality of contact portion 72 and arm 76 into a single body. Other embodiments combine the functionality of several portions of proximal portion 62. As a non-limiting example, in one embodiment contact wire 60 combines the functionality of alignment portion 80 and engaging portion 90 into a single wire segment. Still other embodiments may combine the functionality of wire segment 64 and curve segment 66.

Figure 4:
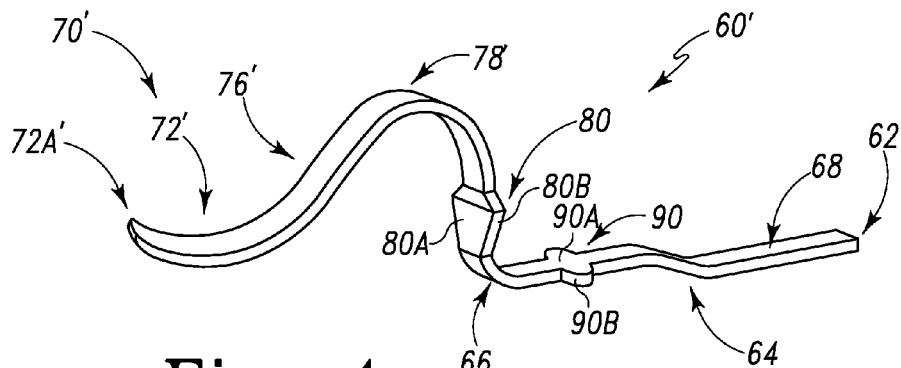
FIG. 4 is a perspective view of a contact wire according to one embodiment of present invention.

As further illustrated in FIG. 4, one embodiment of the present invention comprises contact wire 60' having proximal portion 62 and distal portion 70'. The distal portion 70' includes contact portion 72', contact portion end 72A', arm portion 76', and spring portion 78'. Contact portion 72' provides a curved or spoon-shaped, low-abrasive point of contact between the contact wire 60' and a test strip 40. As described below, the distal portion 70' is used to create a forward-pointing or cantilevered structure relative to the proximal portion 62. Contact portion 72' and arm portion 76' combine to make a convex curve such that the contact portion end 72A' extends substantially in the direction of extraction E. Spring portion 78' and arm portion 76' hold contact portion 72' in position for receiving the test strip. As a further feature, contact portion 72' and contact portion end 72A' may be shaped or extended to minimize abrasion to the test strip during insertion and extraction of the test strip into the testing device.

Figure 5:
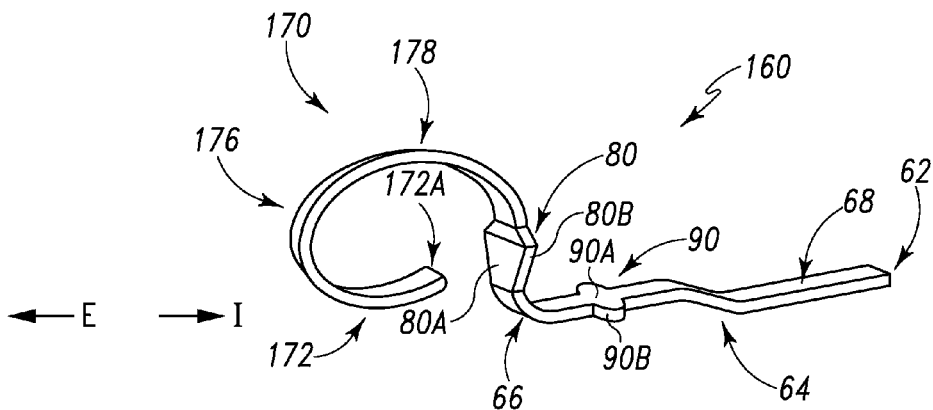
FIG. 5 is a perspective view of a contact wire according to one embodiment of present invention.

As illustrated in FIG. 5, another embodiment of the present invention includes contact wire 160 having a proximal portion 62 and distal portion 170. Distal portion 170 includes contact portion 172, contact portion end 172A, arm portion 176, and spring portion 178. Contact wire 160 is similar in form and function to wire 60, except the functionality of arm portion 176 combines the functions of transition portion 74 (having a convex curvature that causes contact portion end 72A to extend in the direction of insertion I) and arm 76. Otherwise, elements 172, 172A, and 178 of FIG. 5 are analogous in form and function to elements 72, 72A, and 78 of FIG. 3.

It will be appreciated that the contact wires tend to act as springs that can store mechanical energy imparted through friction with a test strip 40. It has been determined by the inventors that friction causes less damage (both to the test strips and the contact wires themselves) when the frictional force is imparted to the contact wires with "dragging" contract, rather than "pushing contact." Thus, the contact wires are preferably formed with a roughly loop-shaped portion, as, for example, contact wire 60 has in distal portion 70. These loop-shaped structures cause the stored energy to be stored throughout a relatively large arc, meaning that little of the spring's force is applied in the direction normal to the test strip 40. Preferably, energy imparted to the contact wire through friction with the test strip 40 is distributed over directions spanning at least 90 degrees. The loop-like form therefore greatly reduces the positive feedback of frictional forces, giving the contact wires less of a tendency to bite or dig in.

Another advantage of contact wires with curved forms like those shown in FIGS. 3-5 is that they are less likely to be deformed by catching on defects in test strips (or even other objects that might be inserted). Because the tip of the contact wire is above the edge of the slot 32, it does not make contact with the test strip, even if there are significant discontinuities in the surface.

Contact wires are advantageously flattened, as shown in FIGS. 3-5. This biases them to deform in the plane perpendicular to the test strip 40 and the direction of insertion I, rather than to the side, where they might come into contact with an adjacent contact wire.

Figure 6:
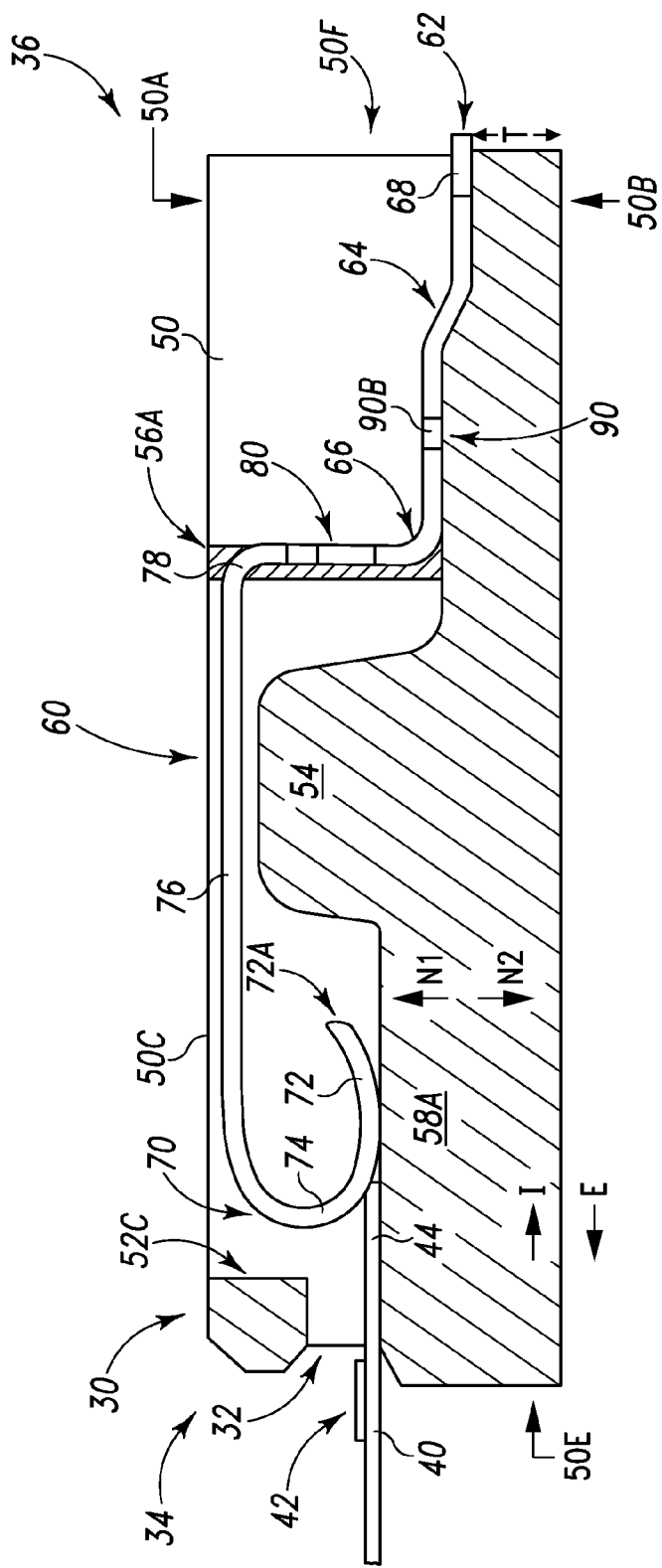
FIG. 6 is a side sectional view of a system according to one embodiment of the present invention.

Turning to FIG. 6, a side cross-sectional view of the assembly 36 is shown. Contact wire 60 forms a reverse cantilever structure anchored by proximal end 62 and has a fulcrum point at spring portion 78. Arm 76 acts as the beam of the cantilever structure supporting contact portion 72 and transition portion 74. Contact portion end 72A serves as the end of the cantilever and points in the direction of the fulcrum point.

Contact wire 60 is held in a substantially fixed orientation relative to connector housing 50 by alignment portion 80 and engaging portion 90. The alignment portion 80 is held in place by protrusions 80A and 80B (see FIG. 3) engaging with assembly features 56A and 56B (see FIG. 2), respectively, of assembly slot 56. Similarly, protrusions 90A and 90B (see FIG. 3) engage wire slot walls 52A and 52B (see FIG. 2), respectively, and hold engaging portion 90 in a substantially fixed position relative to the wire slot walls and to second wire slot floor 58B. As a result, contact portion 72 is thus held in its rest position relative to first wire slot floor 58A.

Generally, the contact portion 72 is initially in its resting position with contact portion 72 touching or near first wire slot floor 58A. As test strip 40 is inserted into the assembly 36, test strip end 44 engages contact wire 60 and deflects contact portion 72 in the normal direction N1 away from its resting position. The deflection creates a force on the contact wire 60 at the point of contact between contact portion 72 and test strip 40 that is substantially in direction N1, which is normal to direction of insertion I. This normal force is translated through transition segment 74 to arm portion 76. Arm portion 76 operates in large part as a lever upon spring portion 78. This allows test strip 40 to pass between the contact wire 60 and first wire slot floor 58A.

Figure 7:
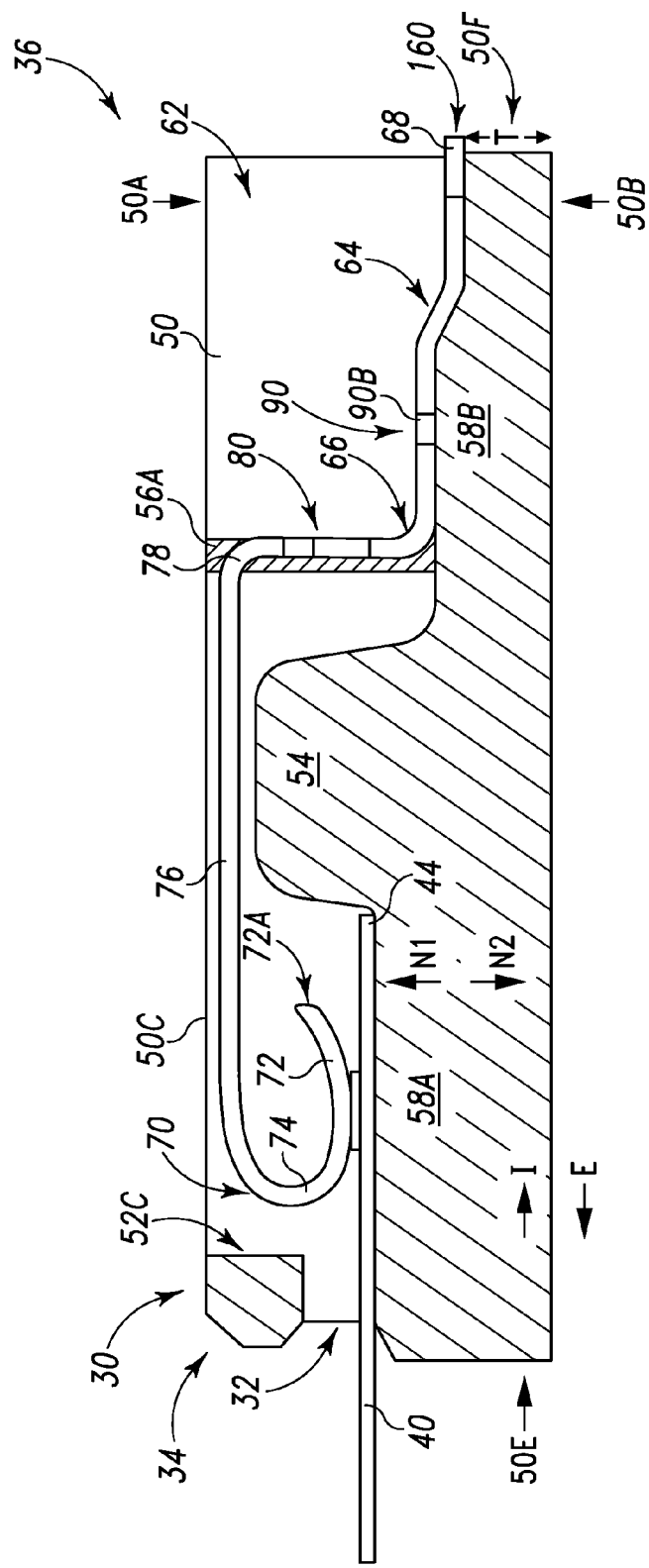
FIG. 7 is a side sectional view of a system according to one embodiment of the present invention.

The stored energy in the spring portion 78, by this normal force in the direction N1, creates a counter-force in normal direction N2 upon test strip 40. This counter-force acts to squeeze test strip 40 between the contact portion 72 and first wire slot floor 58A. Upon full insertion of test strip 40, as shown in FIG. 7, contact portion 72 comes into substantial electrical contact with contact pad 42, and test strip end 44 rests proximate to or in contact with projection 54.

When the test strip 40 is extracted from the test meter 30, the test strip 40 moves substantially in the direction of extraction, E, which is opposite the direction of insertion, I. Spring portion 78 continues to squeeze test trip 40 between contact portion 72 and first wire slot floor 58A until the test strip 40 reaches the initial contact position as shown in FIG. 6. As the test strip 40 continues to move in the direction of extraction E, contact portion 72 returns to its resting position proximal to first wire slot floor 58A. The test strip 40 continues to move in the direction of extraction E until it exits the connector housing 50.

As will be appreciated by those skilled in the art, reducing the normal counter-force applied to test strip 40 consequentially reduces the frictional or abrading forces applied to test strip 40 and contact pad 42. Thus, some embodiments of the present invention adjust the length of arm portion 76 to control the magnitude of the normal force in direction N1 required to overcome the counter-force produced by the spring portion 78. Other embodiments use a technique of controlling the elasticity of spring portion 78 to limit the normal force required at the contact portion 72 to deflect contact wire 60. Still other embodiments employ a combination of arm length and spring elasticity as controlling factors. Some embodiments limit the normal counter-force exerted upon the contact pad 42 to less than 0.4 N. Still other embodiments limit the normal counter-force applied at the contact portion 72 to less than 0.3 N. Other embodiments limit the normal counter-force to between 0.1 N and 0.3 N.

Figure 8:
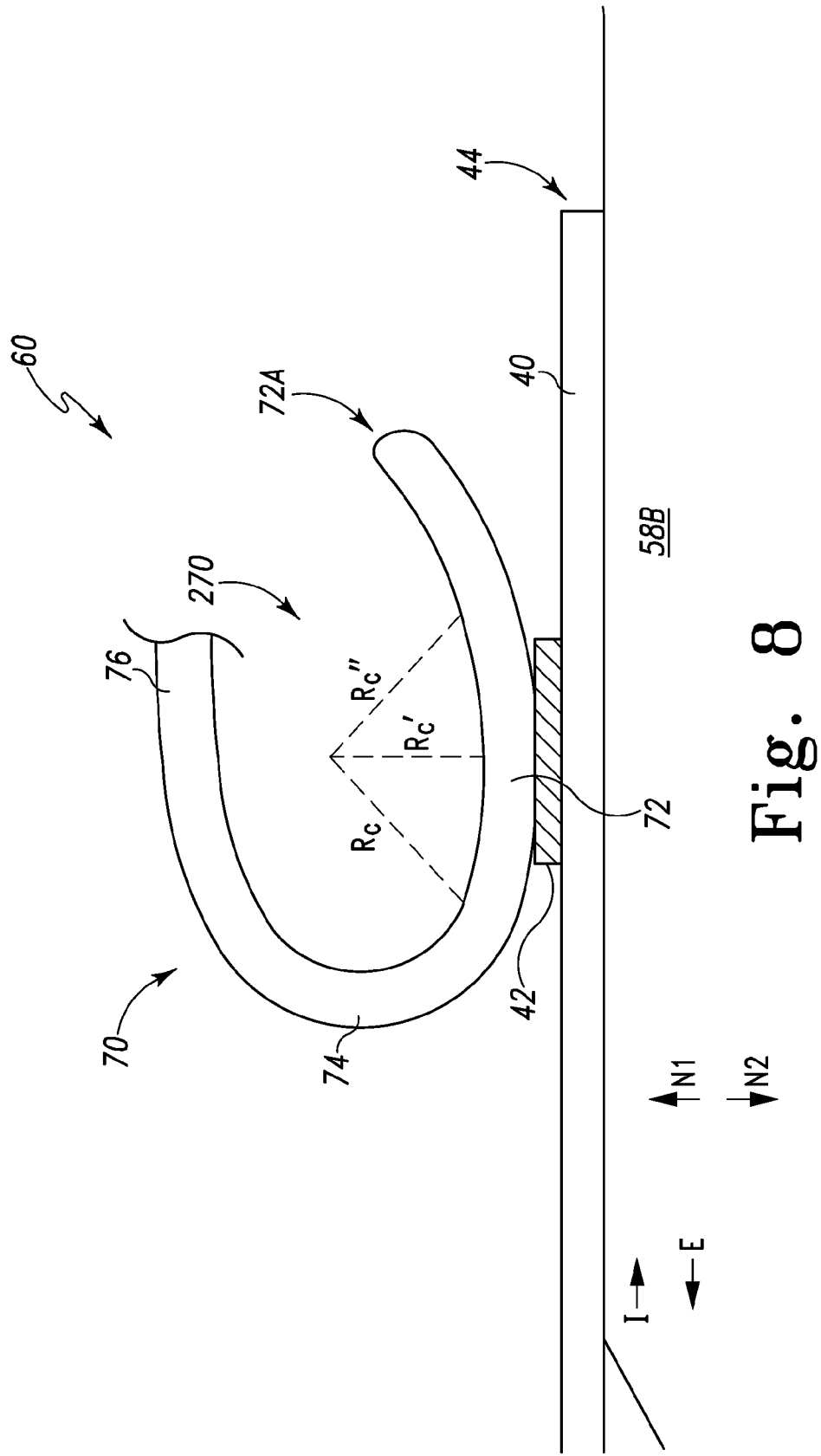
FIG. 8 is a side view of a contact portion of a contact wire in electrical contact with a contact pad in one embodiment of the present invention.

Certain embodiments of the present invention reduce abrasive damage to test strip 40 by controlling the radius of curvature of the contact portion 72. As shown in FIG. 8, the contact wire 60 has a convex shape and includes a contact portion 72 with a radius of curvature $R_C$ measured in a plane parallel to the direction of insertion I and perpendicular to the surface of the contact pad. The effect of increasing the radii of curvature at the points of contact is to lower the abrading force applied per unit area of the test strip 40 (and contact pad 42, which is of particular interest). Additional embodiments of contact wire 60 include techniques and features for smoothing, rounding, and/or extending wire end 72A. Certain of these techniques have the benefit of reducing the abrading force applied to the contact pad 42 and diminishing wear on contact portion 72 and/or contact pad 42.

Certain embodiments include a contact portion 72 having a radius of curvature, $R_C$, greater than 3 mm. In other embodiments, the contact portion has a radius of curvature greater than 4 mm. In still other embodiments, the radius of curvature is greater than 6 mm. In certain embodiments, the radius of curvature can vary over the region of contact portion 72. Illustratively, during insertion and extraction, the test strip 40 may have several points of contact with contact portion 72. Each point of contact may have a different radius of curvature $R_C$, $R_C'$, and $R_C''$; however, at each point of contact with test strip 40, contact portion 72 has a minimum desired radius of curvature.

Figure 9:
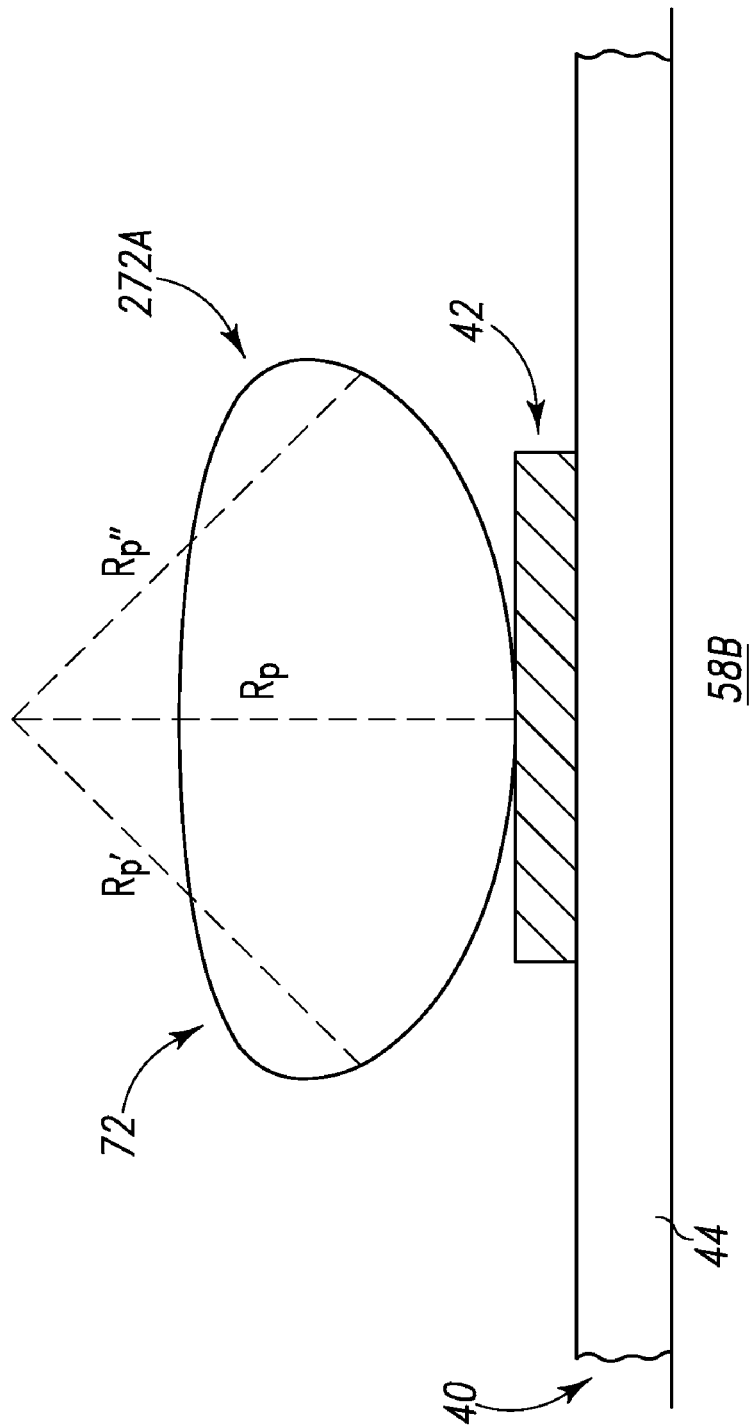
FIG. 9 is a cross-sectional view of a contact portion of a contact wire in electrical contact with a contact pad in one embodiment of the present invention.

As shown in FIG. 9, other embodiments of the present invention further reduce the abrading tendency of the sliding contact between contact wire 60 and test strip 40 by providing and controlling a cross-sectional radius of curvature, $R_P$, of the contact wire 60. As illustrated, the cross-sectional radius of curvature $R_P$ is measured in a plane perpendicular to the direction of insertion I and perpendicular to the plane of the contact pad. In at least one embodiment, $R_P$ is larger than 1 mm. In certain embodiments $R_P$ is greater than 2 mm. Other embodiments have a radius of curvature $R_P$ greater than 4 mm. In still other embodiments, in regions where $R_C=R_P$, the surface of contact wire 60 has a spherical surface quality at the point of contact with contact pad 42. In addition, other embodiments include as a feature end 72A that is rounded or beveled.

Figure 10:
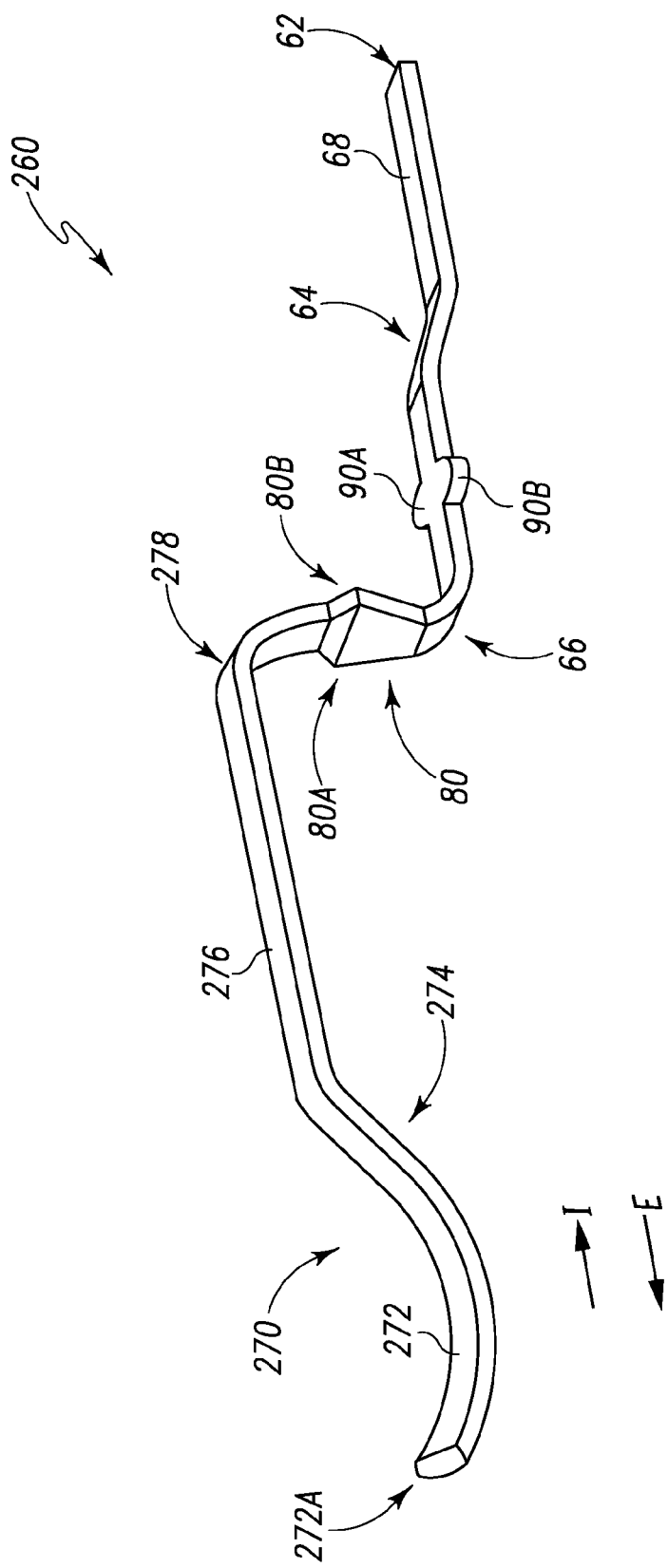
FIG. 10 is a perspective view of a contact wire according to one embodiment of present invention.

As shown in FIG. 10, at least one embodiment of the present invention comprises a contact wire 260 having a proximal portion 62 and distal portion 270. The distal portion 270 includes contact portion 272, of contact portion end 272A, transition segment 274, arm portion 276, and spring portion 278. Contact wire 260 is similar in form and function to wire 60' (see FIG. 4), except the functionality of arm portion 76' (FIG. 4) is divided into transition segment 274, having a concave curvature that causes contact portion end 272A to extend in the direction of extraction E, and arm 276. Otherwise, elements 272, 272A, and 278 of FIG. 10 are analogous in form and function to elements 72', 72A', and 78' of FIG. 4.

The proximal portion 62 of contact wire 260 is held in a substantially fixed position relative to the connector housing 50 by alignment portion 80 and engaging portion 90. Similar to distal portion 70' in FIG. 4, distal portion 270 includes a convex curve that permits contact portion end 272A to extend substantially in the direction of extraction E.

Figure 11:
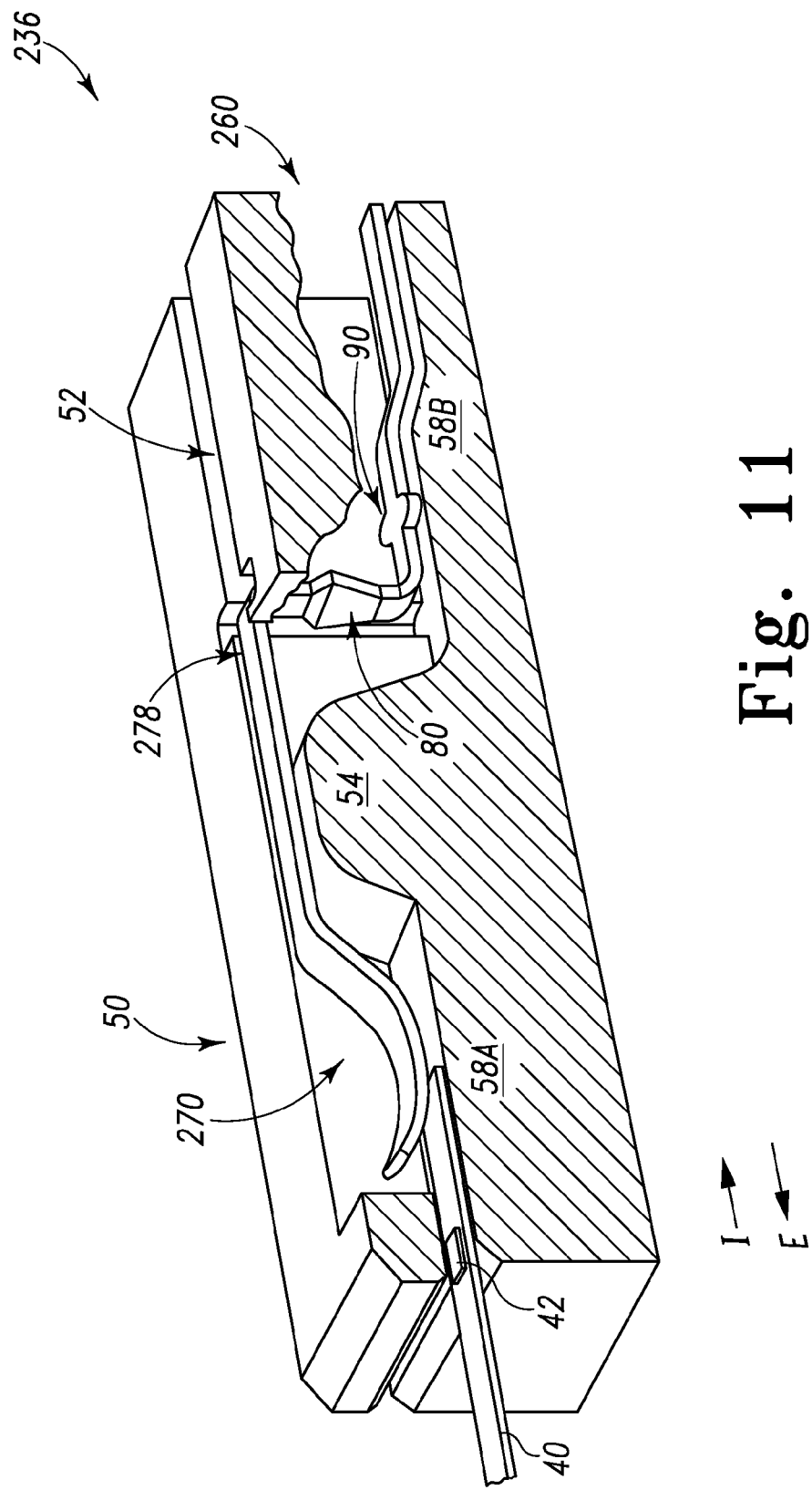
FIG. 11 is sectional view of a system according to one embodiment of the present invention.

As illustrated in FIG. 11, connector assembly 236 includes contact wire 260 (within wire slot 52) and connector housing 50. Similar to assembly 36 of FIG. 6, contact wire 260 is held in a substantially fixed orientation relative to connector housing 50 by alignment portion 80 and engaging portion 90. As a result, distal portion 270 forms a cantilevered structure, with a fulcrum point at spring portion 278, and is held in a rest position over the first wire slot floor 58A.

Figure 12:
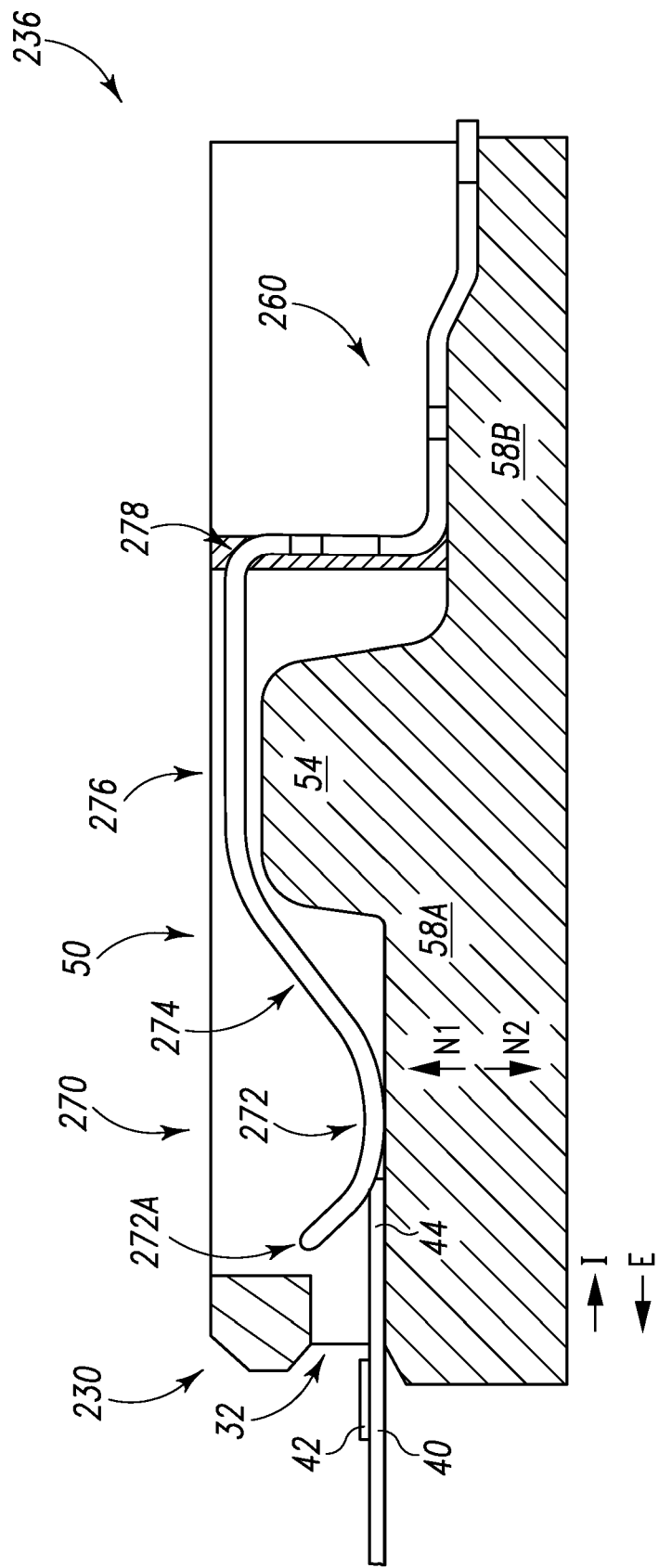
FIG. 12 is a side sectional view of a system according to one embodiment of the present invention.

As shown in FIG. 12, contact portion 272 is initially held in its rest position in substantial proximity to wire slot floor 58A by spring portion 278 until test strip 40 is inserted through slot 32 of the test device 30. As test strip 40 is inserted and comes into contact with the distal portion 270, it creates a normal force in direction N1 acting upon distal portion 270, which force deflects contact portion 272 away from its rest position over wire slot floor 58A. This normal force is transmitted through transverse segment 274 to arm 276 which acts upon spring portion 278.

Figure 13:
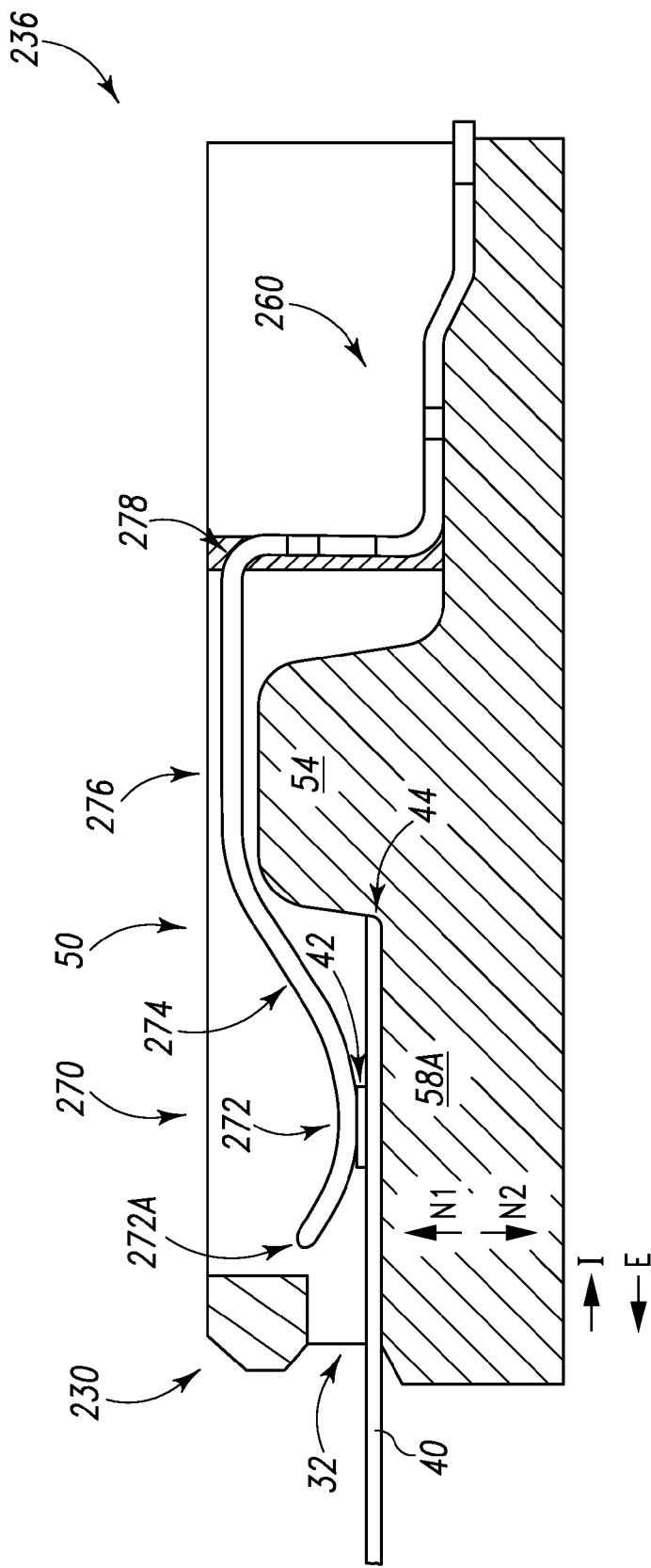
FIG. 13 is a side sectional view of a system according to one embodiment of the present invention.

As illustrated in FIG. 13, the test strip end 44 abuts projection 54 when fully inserted into the test device. Contact portion 272 comes into electrical contact with contact pad 42 while spring portion 278 squeezes the test strip 40 between the contact wire 260 and first wire slot floor 58A. During extraction, test strip 40 moves substantially in the direction of extraction E. Spring portion 278 continues to squeeze test strip 40 between contact portion 272 and first wire slot floor 58A. As test strip 40 moves in the direction of extraction, contact portion 272 returns to its resting position. Test strip 40 continues to move in the direction of extraction E until it exits the connector housing 50.

Figure 14:
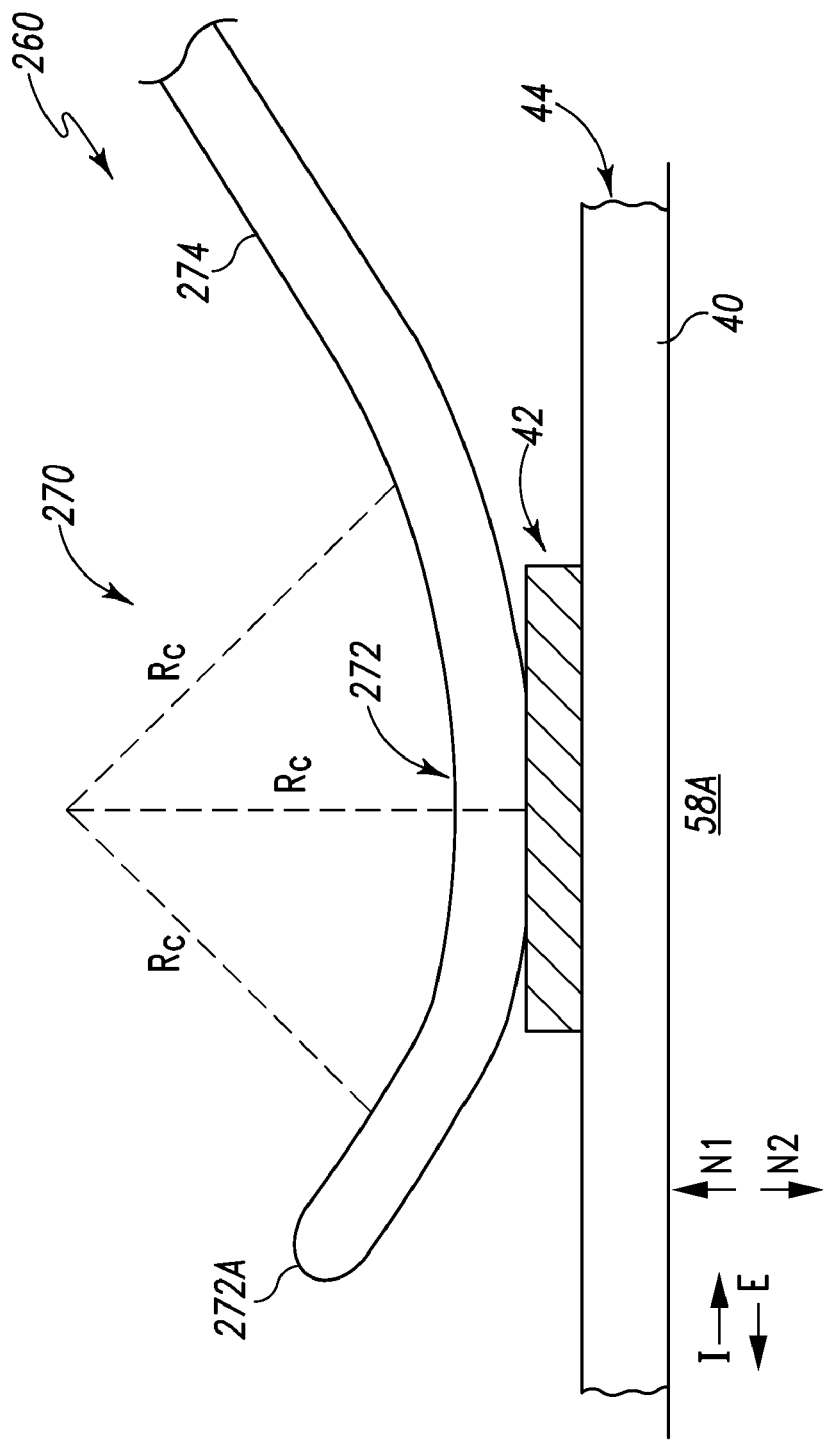
FIG. 14 is a side view of the contact wire at the point of contact in one embodiment of the present invention.

Some embodiments of the present invention, as shown in FIG. 14, include contact wire 260 having a contact portion 272 with a radius of curvature $R_C$ and a cross-sectional radius of curvature $R_P$ (not shown). Similar to contact wire 60 of FIG. 8, increasing the radius of curvature of the contact portion 272 distributes the normal force across a larger area and decreases the abrasions inflicted upon the test strip 40.

Additional embodiments of the present invention include a technique of plating the contact portion with an electrically conductive material that is softer than the material used to form the contact pad 42 on test strip 40. During insertion and extraction of test strip 40, a portion of the soft plating material is sacrificed to reduce the abrasions on the test pad 42. In one non-limiting example, the contact wire is made of phosphor bronze and is plated with Ni/NiPd at the contact surface. Likewise, test strips 40 can be designed so that little or no low-resistance contact metal is scraped off contact pad 42 during insertion and extraction of test strip 40. Additionally, the plating material should be chosen so that the material will not form a cold contact weld with the materials used to form test strip 40 or test pad 42. Illustratively, in one embodiment, the contact pad 42 is gold and is plated with German Silver. As a result, some embodiments include a contact portion plated with a soft conductive material have a minimum radius of curvature $R_C$<1 mm.

A non-limiting list of exemplary plating materials for plating the contact portion of the contact wire includes, but is not limited to, Pd, Ni, NiPd, NiCo, Sn, SnPb, Ag, Cu, Au, and German Silver. Certain embodiments plate the contact portion with non-gold materials. In other embodiments, the plating material has a hardness index KHV50 less than 900. In still other embodiments, the plating material has a hardness index KHV50 between 300 and 650. Alternatively, some embodiments use plating material with a harness index KHV50 between 60 and 300. Other embodiments use a plating material with a hardness index KHV50 between 25 and 60. In still other embodiments, the plating material has a hardness index KHV50 less than 25. In yet other embodiments, the plating material has a hardness index KHV50 less than 20. The plating thickness applied to the contact portion depends upon the desired number of test strip insertions and extractions a testing system is expected to survive. Illustratively, German Silver plated contact wires have a plating thickness between 4 mils and 7 mils. In other embodiments, the contact portion's plating thickness is less than 2 mils, while in still others the contact portion's plating thickness ranges between 0.25 mil and 1.5 mils. See TABLE 1 for a non-limiting chart of potential plating materials and related harnesses and plating thickness.

TABLE 1

| Metal Plating | Hardness (KHV50) | Typical Thickness Ranges in Microns |
|---|---|---|
| Au | 40 soft | flash-2.5 |
| Au | 180-200 hard | flash-2.5 |
| Pd | 400-450 | 0.5-1.25 |
| Pd—Ni | 500-550 | 0.5-1.25 |
| Pd—Co | 600-650 | 0.5-1.25 |
| Sn | 15-25 | 2.5-5 |
| Sn—Pb | 13-20 | 2.5-5 |
| Ag | 40-60 | flash-2.5 |
| Ni | 300 | 1-2.5 |

It has been empirically determined by the inventors that the best compliment to thin film gold is a plating of 20/80 NiPd alloy.

In certain embodiments, an under-plating of copper is used to further decrease friction between the contact pad 42 and the contact portion 40. Copper (like other suitable soft metals) tends to fill gaps, so that an underplating tends to make the contact surfaces smoother. Those skilled in the art will readily recognize that many other types of metals can be used for underplating.

Other embodiments of the present invention include various numbers of contact pads and contact wires. In one non-limiting illustrative example, a connector may include eight contact wires. In some embodiments, the wires are placed in non-staggered row arrangements. In still other embodiments, the wires are placed in staggered row arrangements. As a result, adjacent neighboring wires come into contact with contact pads at various points during insertion process. The staggering approach allows higher pin and contact pad densities as compared to a single-row design.

All publications, prior applications, and other documents cited herein are hereby incorporated by reference in their entirety as if each had been individually incorporated by reference and fully set forth. This application incorporates by reference, in their entireties, U.S. patent application Ser. No. 10/935,522 (entitled BIOLOGICAL TESTING SYSTEM, filed Sep. 7, 2004), SYSTEM AND METHOD FOR ANALYTE MEASUREMENT USING AC EXCITATION (U.S. Provisional Application No. 60/480,298, filed Jun. 20, 2003), METHOD OF MAKING A BIOSENSOR (case number BMID 9958 CIP US, filed Jun. 20, 2003), DEVICES AND METHODS RELATING TO ANALYTE SENSORS (U.S. Provisional Application No. 60/480,397, filed Jun. 20, 2003), and U.S. patent application Ser. No. 10/264,891 (entitled ELECTRODES, METHODS, APPARATUSES COMPRISING MICRO-ELECTRODE ARRAYS, filed Oct. 4, 2002), and U.S. Pat. No. 6,379,513 B1.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A system for measuring an analyte of interest in a biological fluid, comprising:
 a test strip for receiving a sample of the biological fluid and having at least one contact pad formed thereon; and
 a meter having a connector that defines a corridor therein for receiving a portion of the test strip as it moves in a direction of insertion, the connector having at least one contact wire for contacting a surface of a respective one of the at least one contact pads at a respective at least one contact point;
 wherein said at least one contact wire has a proximal portion coupled to said connector and a distal portion, and an arm portion between said proximal portion and said distal portion;
 wherein said arm portion deflects without contacting the corridor in response to insertion of said test strip; and
 wherein said at least one contact wire extends from said proximal portion, and said distal portion includes a contact portion having a radius of curvature to contact the contact pad.

2. The system of claim 1, wherein the contact point of the at least one contact wire has a radius of curvature, in a plane perpendicular to the direction of insertion and perpendicular to the surface of the at least one contact pad, that is at least about 1 mm.

3. The system of claim 1, wherein the contact point of the at least one contact wire has a radius of curvature, in a plane perpendicular to the direction of insertion and perpendicular to the surface of the at least one contact pad, that is at least about 2 mm.

4. The system of claim 1, wherein the contact point of the at least one contact wire has a radius of curvature, in a plane perpendicular to the direction of insertion and perpendicular to the surface of the at least one contact pad, that is at least about 4 mm.

5. The system of claim 1, wherein the contact point of the at least one contact wire has a first radius of curvature, in a plane parallel to the direction of insertion and perpendicular to the surface of the at least one contact pad, that is substantially equal to a second radius of curvature, in a plane perpendicular to the direction of insertion of the test strip and perpendicular to the surface of the at least one contact pad.

6. The system of claim 1, wherein the contact point is made of phosphor bronze.

7. The system of claim 1, wherein the contact point is plated with a material selected from a group consisting of nickel, NiPd, a 20% Ni alloy, Pd, NiCo, Sn, and SnPb.

8. The system of claim 1, wherein the contact point is plated with Ag.

9. The system of claim 1, wherein the contact point is plated with Cu.

10. The system of claim 1, wherein the contact point is plated with Au.

11. The system of claim 1, wherein the contact point is plated with German Silver.

12. The system of claim 1, wherein the contact point is plated with PdCo.

13. The system of claim 1, wherein the contact point is plated with a material having a hardness index KHV50 of less than about 900.

14. The system of claim 1, wherein the contact point is plated with a material having a hardness index KHV50 between about 300 and about 650.

15. The system of claim 1, wherein the contact point is plated with a material having a hardness index KHV50 between about 60 and about 300.

16. The system of claim 1, wherein the contact point is plated with a material having a hardness index KHV50 between about 25 and about 60.

17. The system of claim 1, wherein the contact point is plated with a material having a hardness index KHV50 of less than about 25.

18. The system of claim 1, wherein a force applied by the at least one contact wire to the respective at least one contact pad in a direction normal to the surface of the contact pad is less than about 0.4 N.

19. The system of claim 1, wherein a force applied by the at least one contact wire to the respective at least one contact pad in a direction normal to the surface of the contact pad is less than about 0.3 N.

20. The system of claim 1, wherein a force applied by the at least one contact wire to the respective at least one contact pad in a direction normal to the surface of the contact pad is between about 0.1 N and about 0.3 N.

21. The system of claim 1, wherein the distal portion terminates in a distal end that is configured so as not to contact the test strip during insertion of the test strip into the meter.

22. The system of claim 1, wherein the distal portion is approximately loop-shaped.

23. The system of claim 1, wherein the distal portion is formed such that energy imparted to the contact wire through friction between the contact wire and the test strip produces force in directions distributed through at least 90 degrees.

24. The system of claim 1, wherein the distal portion is formed to avoid positive feedback from friction between the contact wire and the test strip.

25. The system of claim 1, wherein said at least one contact wire extends from said proximal portion, and in said distal portion has a substantially continuous bend into a direction substantially orthogonal to said direction of insertion and then into said direction of insertion, terminating at a distal end.

26. The system of claim 1, wherein the contact point of the at least one contact wire is plated with a metal that does not form a cold contact weld to the respective at least one contact pad of the test strip.

27. The system of claim 26, wherein the contact point is plated with an underplating of copper.

28. The system of claim 1, wherein the contact wire has a radius of curvature at the contact point, taken in a plane parallel to the direction of insertion and perpendicular to the surface of the at least one contact pad, of at least about 3 mm.

29. The system of claim 28, wherein the radius of curvature is at least about 4 mm.

30. The system of claim 28, wherein the radius of curvature is at least about 6 mm.

31. A connector for use in a test meter adapted for use with a biological test strip to measure an analyte of interest, a portion of the test strip being received in an opening and a corridor in the test meter as it moves in a direction of insertion, the test strip when received in the opening having at least one contact pad which engages the connector, the connector comprising:
    at least one contact, the contact comprising a contact wire having a contact portion that makes conductive contact with a contact pad of the test strip,
    wherein said contact wire has a proximal portion and a distal portion, and an arm portion between said proximal portion and said distal portion; and
    wherein said arm portion deflects without contacting the corridor in response to insertion of the test strip; and
    wherein said contact wire extends from said proximal portion, and said distal portion includes the contact portion having a curved shape to engage the contact pad.

32. The connector of claim 31, wherein the contact portion of the at least one contact has a radius of curvature, in a plane parallel to the direction of insertion of the test strip and perpendicular to a surface of the at least one contact pad, that is at least about 3 mm.

33. The connector of claim 31, wherein the contact portion of the at least one contact has a radius of curvature, in a plane parallel to the direction of insertion of the test strip and perpendicular to a surface of the at least one contact pad, that is at least about 4 mm.

34. The connector of claim 31, wherein the contact portion of the at least one contact has a radius of curvature, in a plane parallel to the direction of insertion of the test strip and perpendicular to a surface of the at least one contact pad, that is at least about 6 mm.

35. The connector of claim 31, wherein the contact portion of the at least one contact has a radius of curvature, in a plane perpendicular to the direction of insertion of the test strip and perpendicular to a surface of the at least one contact pad, that is at least about 1 mm.

36. The connector of claim 31, wherein the contact portion of the at least one contact has a radius of curvature, in a plane perpendicular to the direction of insertion of the test strip and perpendicular to a surface of the at least one contact pad, that is at least about 2 mm.

37. The connector of claim 31, wherein the contact portion of the at least one contact has a radius of curvature, in a plane perpendicular to the direction of insertion of the test strip and perpendicular to a surface of the at least one contact pad, that is at least about 4 mm.

38. The connector of claim 31, wherein the contact portion of the at least one contact has a first radius of curvature, in a plane parallel to the direction of insertion of the test strip and perpendicular to a surface of the at least one contact pad, that is substantially equal to a second radius of curvature, in a plane perpendicular to the direction of insertion of the test strip and perpendicular to the surface of the at least one contact pad.

39. The connector of claim 31, wherein the contact portion is made of phosphor bronze.

40. The connector of claim 31, wherein the contact portion is plated with nickel.

41. The connector of claim 31, wherein the contact portion is plated with Pd.

42. The connector of claim 31, wherein the contact portion is plated with NiCo.

43. The connector of claim 31, wherein the contact portion is plated with Sn.

44. The connector of claim 31, wherein the contact portion is plated with SnPb.

45. The connector of claim 31, wherein the contact portion is plated with Ag.

46. The connector of claim 31, wherein the contact portion is plated with Cu.

47. The connector of claim 31, wherein the contact portion is plated with Au.

48. The connector of claim 31, wherein the contact portion is plated with German Silver.

49. The connector of claim 31, wherein the contact portion is plated with PdCo.

50. The connector of claim 31, wherein the contact portion is plated with a material having a hardness index KHV50 of less than about 900.

51. The connector of claim 31, wherein the contact portion is plated with a material having a hardness index KHV50 between about 300 and about 650.

52. The connector of claim 31, wherein the contact portion is plated with a material having a hardness index KHV50 between about 60 and about 300.

53. The connector of claim 31, wherein the contact portion is plated with a material having a hardness index KHV50 between about 25 and about 60.

54. The connector of claim 31, wherein the contact portion is plated with a material having a hardness index KHV50 of less than about 25.

55. The connector of claim 31, wherein a force applied by the at least one contact wire to the respective at least one contact pad in a direction normal to a surface of the contact pad is less than about 0.4 N.

56. The connector of claim 31, wherein a force applied by the at least one contact wire to the respective at least one contact pad in a direction normal to a surface of the contact pad less than about 0.3 N.

57. The connector of claim 31, wherein a force applied by the at least one contact wire to the respective at least one contact pad in a direction normal to a surface of the contact pad is between about 0.1 N and about 0.3 N.

58. The connector of claim 31, wherein the at least one contact wire is configured such that the distal portion includes a distal end, wherein the distal end is positioned so as not to contact the test strip.

59. The connector of claim 31, wherein the distal portion is approximately loop-shaped.

60. The connector of claim 31, wherein the distal portion is formed such that energy imparted to the contact wire through friction between the contact wire and the test strip produces force in directions distributed through at least 90 degrees.

61. The connector of claim 31, wherein the distal portion is configured to avoid positive feedback from friction between the contact wire and the test strip.

62. The connector of claim 31, wherein said at least one contact wire extends from said proximal portion, and in said distal portion has a substantially continuous bend into a direction substantially orthogonal to said direction of insertion and then into said direction of insertion, terminating at a distal end.

63. The connector of claim 31, wherein the contact portion of the at least one contact is plated with a metal that does not form a cold contact weld to the respective at least one contact pad of the test strip.

64. The connector of claim 61, wherein the contact portion has an underplating of copper.

65. The connector of claim 31, wherein the contact portion is plated with NiPd.

66. The connector of claim 65, wherein the NiPd is a 20% Ni alloy.

67. A test meter adapted for use with a biological test strip to measure an analyte of interest and having at least one contact pad formed thereon, the test meter comprising:
a housing having a slot and a corridor therein for receiving a portion of the test strip; and
a connector disposed at least partially within the housing, the connector comprising:
an opening for receiving at least a portion of the test strip as the test strip moves in a direction of insertion; and
at least one contact wire disposed in the opening, the at least one contact wire having a contact portion that makes electrical contact with a respective one of the at least one contact pad of the test strip;
wherein said at least one contact wire has a proximal portion and a distal portion, and an arm portion between said proximal portion and said distal portion;
wherein said arm portion deflects without contacting the corridor as the test strip moves in direction of insertion; and
wherein said at least one contact wire extends from said proximal portion, and said distal portion includes the contact portion having a radius of curvature to engage the contact pad.

68. The test meter of claim 67, wherein the contact portion of the at least one contact wire has a radius of curvature, in a plane parallel to a direction of insertion of the test strip and perpendicular to a surface of the at least one contact pad, that is at least about 4 mm.

69. The test meter of claim 67, wherein the contact portion of the at least one contact wire has a radius of curvature, in a plane parallel to a direction of insertion of the test strip and perpendicular to a surface of the at least one contact pad, that is at least about 6 mm.

70. The test meter of claim 67, wherein the contact portion of the at least one contact wire has a radius of curvature, in a plane perpendicular to a direction of insertion of the test strip and perpendicular to a surface of the at least one contact pad, that is at least about 1 mm.

71. The test meter of claim 67, wherein the contact portion of the at least one contact wire has a radius of curvature, in a plane perpendicular to a direction of insertion of the test strip and perpendicular to a surface of the at least one contact pad, that is at least about 2 mm.

72. The test meter of claim 67, wherein the contact portion of the at least one contact wire has a radius of curvature, in a plane perpendicular to a direction of insertion of the test strip and perpendicular to a surface of the at least one contact pad, that is at least about 4 mm.

73. The test meter of claim 67, wherein the contact portion of the at least one contact wire has a first radius of curvature, in a plane parallel to a direction of insertion of the test strip and perpendicular to a surface of the at least one contact pad, that is substantially equal to a second radius of curvature, in a plane perpendicular to the direction of insertion of the test strip and perpendicular to the surface of the at least one contact pad.

74. The test meter of claim 67, wherein the contact portion of the at least one contact wire is plated with a metal that does not form a cold contact weld to the respective at least one contact pad of the test strip.

75. The test meter of claim 67, wherein the contact portion has an underplating of copper.

76. The test meter of claim 67, wherein the contact portion is made of phosphor bronze.

77. The test meter of claim 67, wherein the contact portion is plated with nickel.

78. The test meter of claim 67, wherein the contact portion is plated with NiPd.

79. The test meter of claim 67, wherein the contact portion is plated with a 20% Ni alloy.

80. The test meter of claim 67, wherein the contact portion is plated with Pd.

81. The test meter of claim 67, wherein the contact portion is plated with NiCo.

82. The test meter of claim 67, wherein the contact portion is plated with Sn.

83. The test meter of claim 67, wherein the contact portion is plated with SnPb.

84. The test meter of claim 67, wherein the contact portion is plated with Ag.

85. The test meter of claim 67, wherein the contact portion is plated with Cu.

86. The test meter of claim 67, wherein the contact portion is plated with Au.

87. The test meter of claim 67, wherein the contact portion is plated with German Silver.

88. The test meter of claim 67, wherein the contact portion is plated with PdCo.

89. The test meter of claim 67, wherein the contact portion is plated with a material having a hardness index KHV50 of less than about 900.

90. The test meter of claim 67, wherein the contact portion is plated with a material having a hardness index KHV50 between about 300 and about 650.

91. The test meter of claim 67, wherein the contact portion is plated with a material having a hardness index KHV50 between about 60 and about 300.

92. The test meter of claim 67, wherein the contact portion is plated with a material having a hardness index KHV50 between about 25 and about 60.

93. The test meter of claim 67, wherein the contact portion is plated with a material having a hardness index KHV50 of less than about 25.

94. The test meter of claim 67, wherein a force applied by the at least one contact wire to the respective at least one contact pad in a direction normal to a surface of the contact pad is less than about 0.4 N.

95. The test meter of claim 67, wherein a force applied by the at least one contact wire to the respective at least one contact pad in a direction normal to a surface of the contact pad less than about 0.3 N.

96. The test meter of claim 67, wherein a force applied by the at least one contact wire to the respective at least one contact pad in a direction normal to a surface of the contact pad is between about 0.1 N and about 0.3 N.

97. The connector of claim 67, wherein the at least one contact wire is configured such that the distal portion terminates in a distal end that is positioned so as not to contact the test strip.

98. The connector of claim 67, wherein the distal portion is approximately loop-shaped.

99. The connector of claim 67, wherein the distal portion is formed such that energy imparted to the contact wire through friction between the contact wire and the test strip produces force in directions distributed through at least 90 degrees.

100. The connector of claim 67, wherein the distal portion is configured to avoid positive feedback from friction between the contact wire and the test strip.

101. The test meter of claim 67, wherein the radius of curvature is in a plane parallel to a direction of insertion of the test strip and perpendicular to a surface of the at least one contact pad, the radius of curvature is at least about 3 mm.

102. The test meter of claim 67, wherein said at least one contact wire extends from said proximal portion, and in said distal portion has a substantially continuous bend into a direction substantially orthogonal to said direction of insertion and then into said direction of insertion, terminating at a distal end.

103. A system for measuring an analyte of interest in a biological fluid, comprising:
a test strip for receiving a sample of the biological fluid and having at least one contact pad formed thereon; and
a meter having a connector for receiving the test strip as the test strip moves in a direction of insertion, the connector having a housing and at least one contact wire for contacting a respective one of the at least one contact pads at a respective at least one contact point;
wherein said at least one contact wire has a proximal end, a distal end, and an arm portion positioned between the proximal end and the distal end;
wherein the arm portion is mounted such that the arm portion deflects without contacting the housing when receiving the test strip; and
wherein the contact wire includes a contact portion adjacent the distal end, the contact portion having a curved shape to contact the contact pad.

104. The system of claim 103, wherein the distal end is formed such that energy imparted to the contact wire through friction between the contact wire and the test strip produces force in directions distributed through at least 90 degrees.

105. The system of claim 103, wherein the distal end is formed to avoid positive feedback from friction between the contact wire and the test strip.

106. The system of claim 103, wherein said at least one contact wire extends from said proximal end, bends in a direction substantially orthogonal to said direction of insertion then bends again in said direction of insertion, terminating at the distal end.

107. A connector for use in a test meter adapted for use with a biological test strip to measure an analyte of interest, a portion of the test strip being received in an opening and a corridor in the test meter as the test strip moves in a direction of insertion, the test strip when received in the opening having at least one contact pad which engages the connector, the connector comprising:
at least one contact, the contact comprising a contact wire having a contact portion that makes conductive contact with the contact pad of the test strip,
wherein said at least one contact wire has a first and second side, a proximal portion, a distal portion, and an arm portion positioned between said proximal portion and said distal portion, the distal portion including the contact portion having a curved shape to contact the contact pad; and
wherein said arm portion deflects without contacting the corridor in response to insertion of the test strip.

108. The connector of claim 107, wherein the distal portion includes a distal end that is formed such that energy imparted to the contact wire through friction between the contact wire and the test strip produces force in directions distributed through at least 90 degrees.

109. The connector of claim 107, wherein the distal portion includes a distal end that is formed to avoid positive feedback from friction between the contact wire and the test strip.

110. The connector of claim 107, wherein said at least one contact wire extends from said proximal portion, bends in a direction substantially orthogonal to said direction of insertion then bends again in said direction of insertion, terminating at a distal end; and wherein each of said bends in said arm portion and distal portion has a radius of curvature measured to said first side when said connector is unengaged with the test strip.

* * * * *